United States Patent [19]

Rosenberg

[11] Patent Number: 4,800,901
[45] Date of Patent: Jan. 31, 1989

[54] BALLOON-TYPE TISSUE EXPANSION DEVICE

[76] Inventor: Lior Rosenberg, 13 Harduff Street, Omer, Beersheva, Israel

[21] Appl. No.: 94,619

[22] Filed: Sep. 9, 1987

[51] Int. Cl.⁴ .............................................. A61B 19/00
[52] U.S. Cl. .................................... 128/899; 128/344; 623/11
[58] Field of Search ................................. 604/96–100; 128/1 R, 344, 899; 623/8, 11, 12

[56] References Cited

U.S. PATENT DOCUMENTS

| | | | |
|---|---|---|---|
| 3,753,439 | 8/1973 | Brugarolas | 604/43 |
| 3,823,720 | 7/1974 | Tribble | 604/43 |
| 4,217,889 | 8/1980 | Radovan et al. | 128/1 R |
| 4,600,015 | 7/1986 | Evans et al. | 604/100 X |
| 4,685,447 | 8/1987 | Iversen et al. | 128/1 R |

Primary Examiner—Dalton L. Truluck
Attorney, Agent, or Firm—Benjamin J. Barish

[57] ABSTRACT

A balloon-type Tissue expander device is provided that has a main balloon portion for stretching tissue when implanted under the skin. The expander balloon includes an inflation conduit and a separate drain tube connected thereto serving to drain fluid accumulating around the balloon away from the implant site. Also an irrigation tube can be included with the drain tube. Finally a pressure transducer is provided to measure pressure within the balloon.

17 Claims, 1 Drawing Sheet

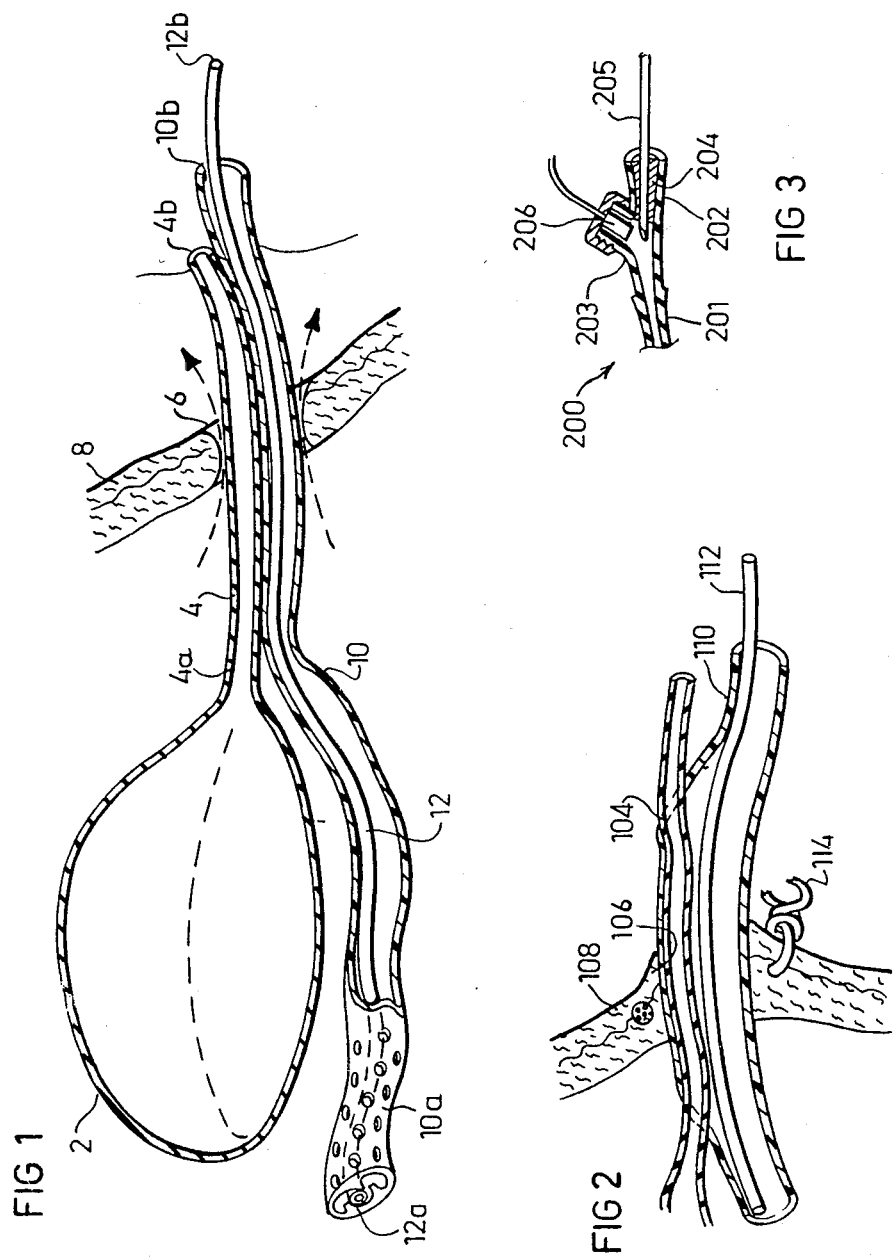

BALLOON-TYPE TISSUE EXPANSION DEVICE

BACKGROUND OF THE INVENTION

The present invention relates to tissue expansion devices, and particularly to such expansion devices of the balloon type.

"Tissue expansion" is the term generally used to describe the increase in tissue dimensions under the influence of mechanical forces. This phenomenon occurs naturally in pregnancy, weight gain, tumour growth and the like. It has been applied in various forms for generations, e.g., lip stretching of certain African women and neck stretching of certain Asian women. In 1957, Charles G. Newman, in the publication "The Expansion of an Area of Skin by Progressive Distension of a Subcutaneous Balloon"; Plast. & Reconst. Surg. 19:124, 1957, described the use of this technique to gain skin for an ear reconstruction; this was done by implanting subcutaneously a rubber balloon and progressively inflating it through an external transcutaenous inflatable tube using a three-way stopcock to achieve expansion of the respective area of the skin. In 1976, Radovan, in the publication "Adjacent Flaps Development Using Expandable Silastic Implants", Annual meeting of the American Society of Plastic and Reconstructive Surgeons, Boston, Mass. Sept. 30, 1976, described the use of this method as a means for adjacent flap development. Since then, tissue expansion and tissue expanders have been commonly used in many body areas in a variety of situations and for numerous reasons, e.g., in the preparation of pockets for mammary or other permanent prosthetics.

The tissue expanders commonly used today include an inflatable balloon connected, usually through an inflation tube, to an inflation reservoir having a self-sealing injection-port, all implanted under the skin. The transcutaneous injection port is periodically injected via a hypodermic needle with a quantity of saline fluid in order to inflate the balloon. However, the use of the present subcutaneous self-sealing injection port for inflating the expander may lead to several rather frequent complications, such as erosion of tissues by the hard injection port, leaking from numerous needle punctures with seroma formation and infection, accidental injection into surrounding tissues through the injection port or into its gel-filled double lumen, and difficulty in implanting and removing the reservoir-port.

An object of the present invention is to provide a tissue expansion device having advantages in the above respects.

SUMMARY OF THE INVENTION

According to the present invention, there is provided a tissue expansion device comprising an inflatable balloon adapted to be implanted subcutaneously, and an inflation tube having one end connected to the balloon to be implanted subcutaneously therewith, with its opposite end to extend through an opening in the skin and to serve as an external entry port for the inflating fluid. The device further includes a drain tube connected to the inflation tube so as to be implanted therewith, with one end of the drain tube to be located adjacent to the implanted inflatable balloon, and the opposite end of the drain tube passing through the opening in the skin to serve as an external port for draining fluid accumulating at the site of implantation of the inflatable balloon.

According to another preferred feature, the device further includes an irrigation tube connected to the drain tube so as to be implantable therewith with one end of the irrigation tube to be located in the site of implantation of the inflatable balloon, and the opposite end of the irrigation tube passing through the opening in the skin to serve as an external port for introducing an irrigating liquid into the site of implantation of the inflatable balloon. Preferably, the irrigating tube is of smaller diameter than, and extends within, the drain tube.

Two embodiments of the invention are described below for purposes of example: In one described embodiment the drain tube is joined to the inflation tube along its length passing through the opening in the skin; more particularly, the drain tube is joined to the inflation tube by a bond which permits manual separation of the end of the drain tube from the inflation tube at the implantation site. In the second described embodiment, the inflation tube is enclosed within the drain tube along the length of both passing through the skin opening.

According to another feature of the present invention, the device further includes a fitting comprising a connector at one end attachable to the external entry port of the inflation tube; a self-sealing plug penetratable by a hypodermic needle for injecting fluid via the connector and inflation tube into the inflatable balloon; and a pressure transducer communicating with the connector for measuring the pressure within the inflatable balloon via the inflation tube.

Preferably, the fitting is a multi-port fitting, having one port serving as the connector, a second port carrying the self-sealing plug, and a third port carrying the pressure transducer.

A tissue expansion device constructed in accordance with the foregoing features avoids or reduces the above-discussed drawbacks of the presently used tissue expanders. In addition, it provides a reliable connection with the implanted balloon for inflation and for monitoring its internal pressure; it provides drainage of the subcutaneous pocket with a minimal ascending contamination; and it provides irrigation of the subcutaneous pocket and particularly the interface between the tissue and the inflatable balloon.

Further, the novel tissue expander obviates the needs for the patient to visit his physician for the transcutaneous injections since the inflation can be carried at the patient's residence by his general practitioner, nurse, paramedic, trained person, or in some selected cases by a relative or the patient himself. This reduces substantially the expense involved in the treatment and the stress on the part of the patient. It also permits a regimen of more frequent injections which reduces the need to apply extreme stretching forces on the skin during each injection, thereby preventing tissue damage, more efficiently exploiting the visco-elastic properties of the skin and further reducing patient stress.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates one form of tissue expansion device constructed in accordance with the present invention;

FIG. 2 is a fragmentary view illustrating another tissue expansion device constructed in accordance with the present invention; and FIG. 3 illustrates a fitting which may be used in the tissue expansion device of either FIGS. 1 or 2.

DESCRIPTION OF PREFERRED EMBODIMENTS

The tissue expansion device illustrated in FIG. 1 comprises an inflatable balloon 2 adapted to be implanted subcutaneously, and an inflation tube 4 having one end 4a connected to balloon 2 so as to be implanted subcutaneously therewith. The opposite end 4b of inflation tube 4 is to extend through an opening 6 in the skin to serve as an external entry port for the inflating fluid.

The illustrated tissue expansion device further includes a drain tube 10 and an irrigation tube 12. End 10a of the drain tube, and end 12a of the irrigation tube, are both implantable subcutaneously with the balloon 2. The opposite end 12b of the irrigation tube 12, and the opposite end 10b of the drain tube 10 are extended with the inflation tube 4 through opening 6 in the skin to serve as external ports for applying irrigation fluid to the implantation site, and for draining the fluid from the implantation site, respectively.

In the arrangement illustrated in FIG. 1, irrigation tube 12 is of substantially smaller diameter than drain tube 10 and is enclosed within the drain tube. Drain tube 10 is joined to inflation tube 4 by a relatively weak bond, such as glue, sufficient to hold the drain tube joined to the inflation tube along the length of the latter tube passing through opening 6 in the skin, but to permit the surgeon to separate the end of the drain tube from the inflation tube and to locate end 10a of the drain tube as desired for draining the fluids accumulating at the implantation site. Part of the fluid drains via the drain tube 10, and part drains by capillary and surface-tension forces along the outer surfaces of both the inflation tube 4 and drain tube 10 as shown by the arrows in FIG. 1.

As one example, inflatable balloon 2 and inflation tube 4 may be made of a soft silicone polymer; drain tube 10 may be a Jackson Pratt type drain also made of a soft silicone polymer and having a length greater than the expanded diameter of balloon 2 (drain tube 10 may be shortened by the surgeon during the procedure as required); and irrigation tube 12 may be a polyvinyl chloride tube of 1 mm inner diameter. Irrigation tube 12 may have a Luer connection to the irrigation syringe/ampule (not shown). Drain tube 4 may be connected to a connecting bag for a vacuum suction.

FIG. 2 illustrates a modification in the construction of the tissue-expansion device. Thus, whereas in the arrangement of FIG. 1 the drain tube 10 was joined to the outer face of the inflation tube 4 along the portion of the inflation tube passing through the skin opening 106 in the arrangement of FIG. 2 the inflation tube 104 is enclosed within the drain tube 110 at the point both tubes pass through the opening 106 in the skin 108. The irrigation tube 112, like the arrangement illustrated in FIG. 1, passes through the drain tube 110 for the complete length of the drain tube.

The FIG. 2 arrangement thus provides a single tube, namely drain tube 110, passing through the skin opening. This allows a cutaneous purse-string suture 114 to be placed around the skin opening 106, in order to constrict the skin around the drain tube 110 and thereby to minimize ascending contamination. The portion of drain tube 110 passing through the skin opening 106 may be of a material compatible with cellular growth, such as "Teflon" (Reg. T.M.) or a carbon fiber mesh.

FIG. 3 illustrates a fitting, generally designated 200, which may be used for inflating the inflation bag, e.g., bag 2, and for measuring the pressure therein. Fitting 200 is a multi-port fitting of Y- or T-configuration, including a first port 201 in the form of a connector connectable to the external end 4b of the inflation tube 4 (or 104), a second port 202, and a third port 203. Port 202 includes a plug 204 of a self-sealing material penetratable by a hypodermic syringe needle 205 for injecting saline solution for inflating bag 2 via the inflation tube; and port 203 includes an electrical pressure-transducer for measuring the pressure within the bag.

While the invention has been described with respect to two preferred embodiments, it will be appreciated that many other variations, modifications and applications of the invention may be made.

What is claimed is:

1. A tissue expansion device, comprising:
   an inflatable balloon adapted to be implanted subcutaneously,
   and an inflation tube having one end connected to said balloon to be implanted subcutaneously therewith, with its opposite end to extend through an opening in the skin and to serve as an external entry port for the inflating fluid;
   characterized in that said device further includes:
   a drain tube connected to said inflation tube so as to be implanted therewith, with one end of the drain tube to be located adjacent to the implanted inflatable balloon, and the opposite end of the drain tube passing through said opening in the skin to serve as an external port for draining fluid accumulating at the site of implantation of the inflatable balloon.

2. The device according to claim 1, further including:
   an irrigation tube connected to said drain tube so as to be implantable therewith with one end of the irrigation tube to be located in the site of implantation of the inflatable balloon, and the opposite end of the irrigation tube passing through the opening in the skin to serve as an external port for introducing an irrigating liquid into the site of implantation of the inflatable balloon.

3. The device according to claim 2, wherein said irrigation tube is of smaller diameter than, and extends within, said drain tube.

4. The device according to claim 1, wherein said drain tube is joined to the inflation tube along the length thereof passing through the opening in the skin.

5. The device according to claim 4, wherein said drain tube is joined to the inflation tube by a bond which permits manual separation of the end of the drain tube from the inflation tube at the implantation site.

6. The device according to claim 1, wherein said inflation tube is enclosed within the drain tube along the length of both passing through the skin opening.

7. The device according to claim 1, further including a fitting comprising:
   a connector at one end attached to the external entry port of the inflation tube;
   a self-sealing plug penetratable by a hypodermic needle for injecting fluid via said connector and inflation tube into the inflatable balloon; and
   a pressure transducer communicating with said connector for measuring the pressure within said inflatable balloon via said inflation tube.

8. A tissue expansion device comprising:

an inflatable balloon adapted to be implanted subcutaneously;

and an inflation tube having one end connected to said balloon to be implanted subcutaneously therewith, with its opposite end to extend through an opening in the skin to serve as an external entry port for the inflating fluid;

characterized in that said device further includes a multi-port fitting comprising:

a first port including a connector at one end attachable to the external entry port of the inflation tube;

a second port including a self-sealing plug penetratable by a hypodermic needle for injecting fluid via said connector and inflation tube into the inflatable balloon; and a third port;

and a pressure transducer connected to said third port and communicating with said connector for measuring the pressure within said inflatable balloon via said inflation tube.

9. The device according to claim 8, wherein said pressure transducer is an electrical transducer mounted in said third port.

10. A tissue expansion device, comprising:

an inflatable balloon adapted to be implanted subcutaneously;

an inflation tube having one end connected to said balloon to be implanted subcutaneously therewith, with its opposite end to extend through an opening in the skin and to serve as an external entry port for the inflating fluid;

a drain tube associated with said inflatable balloon and inflation tube so as to be implanted therewith, with one end of the drain tube to be located adjacent to the implanted inflatable balloon, and the opposite end of the drain tube passing through said opening in the skin to serve as an external port for draining fluid accumulating at the site of implantation of the inflatable balloon; and an irrigation tube associated with said drain tube so as to be implantable therewith with one end of the irrigation tube to be located in the site of implantation of the inflatable balloon, and the opposite end of the irrigation tube passing through the opening in the skin to serve as an external port for introducing an irrigating liquid into the site of implantation of the inflatable balloon.

11. The device according to claim 10, wherein said irrigation tube is of smaller diameter than, and extends within, said drain tube.

12. The device according to claim 10, wherein said drain tube is joined to the inflation tube along the length thereof passing through the opening in the skin.

13. The device according to claim 12, wherein said drain tube is joined to the inflation tube by a bond which permits separation of the end of the drain tube from the inflation tube at the implantation site.

14. The device according to claim 10, wherein said inflation tube is enclosed within the drain tube along the length of both passing through the skin opening.

15. The device according to claim 10, further including a fitting comprising:

a connector at one end attached to the external entry port of the inflation tube;

a self-sealing plug penetratable by a hypodermic needle for injecting fluid via said connector and inflation tube into the inflatable balloon; and a pressure transducer communicating with said connector for measuring the pressure within said inflatable balloon via said inflation tube.

16. The device according to claim 15, wherein said fitting is a three-port fitting, having one port serving as said connector, a second port carrying said self-sealing plug, and a third port carrying said pressure transducer.

17. The device according to claim 16, wherein said pressure transducer is an electrical transducer mounted in said third port.

* * * * *